United States Patent
Borsook et al.

(10) Patent No.: US 12,193,814 B2
(45) Date of Patent: Jan. 14, 2025

(54) ONGOING PAIN DETECTION SYSTEM AND METHOD FOR UTILIZING NEAR-INFRARED SPECTROSCOPY

(71) Applicant: Children's Medical Center Corporation, Boston, MA (US)

(72) Inventors: David Borsook, Concord, MA (US); Ke Peng, Boston, MA (US)

(73) Assignee: Children's Medical Center Corporation, Boston, MA (US)

(*) Notice: Subject to any disclaimer, the term of this patent is extended or adjusted under 35 U.S.C. 154(b) by 907 days.

(21) Appl. No.: 17/275,933

(22) PCT Filed: Sep. 11, 2019

(86) PCT No.: PCT/US2019/050626
§ 371 (c)(1),
(2) Date: Mar. 12, 2021

(87) PCT Pub. No.: WO2020/056011
PCT Pub. Date: Mar. 19, 2020

(65) Prior Publication Data
US 2022/0104738 A1 Apr. 7, 2022

Related U.S. Application Data

(60) Provisional application No. 62/730,269, filed on Sep. 12, 2018.

(51) Int. Cl.
*A61B 5/1455* (2006.01)
*A61B 5/00* (2006.01)
*A61B 5/145* (2006.01)

(52) U.S. Cl.
CPC ........ *A61B 5/14553* (2013.01); *A61B 5/0042* (2013.01); *A61B 5/0075* (2013.01); *A61B 5/14546* (2013.01); *A61B 5/4824* (2013.01); *A61B 5/483* (2013.01); *A61B 2505/05* (2013.01)

(58) Field of Classification Search
CPC . A61B 5/14553; A61B 5/0042; A61B 5/0075; A61B 5/14546; A61B 5/4824; A61B 5/483; A61B 2505/05
See application file for complete search history.

(56) References Cited

U.S. PATENT DOCUMENTS

| | | | |
|---|---|---|---|
| 2004/0243021 A1* | 12/2004 | Murphy | A61B 5/4893 600/549 |
| 2012/0010484 A1* | 1/2012 | Ishikawa | A61B 5/14553 600/310 |
| 2016/0015316 A1* | 1/2016 | Borsook | A61B 5/14546 600/475 |

OTHER PUBLICATIONS

R.R. Nir et al., "Pain assessment by continuous EEG: Association between subjective perception of tonic pain and peak frequency of alpha oscillations during stimulation and at rest", Brain Research, 1344 (2010), pp. 77-86.

* cited by examiner

*Primary Examiner* — Devin B Henson
*Assistant Examiner* — Jonathan M Haney
(74) *Attorney, Agent, or Firm* — Greenberg Traurig, LLP; Melissa Hunter-Ensor; Joshua I. Rudawitz (57) ABSTRACT

An ongoing pain detection system and method are provided. The method includes obtaining imaging data from patient using functional near-infrared spectroscopy from at least one cortical region of the brain of a non-responsive patient and observing power spectral density variations in the signal. The measured imaging data is compared with patient pain based on control data to recognize ongoing pain in the non-responsive patient.

20 Claims, 8 Drawing Sheets

ONGOING PAIN DETECTION SYSTEM AND METHOD FOR UTILIZING NEAR-INFRARED SPECTROSCOPY

CROSS-REFERENCE TO RELATED APPLICATION

This application is a National Stage Application filed under 35 U.S.C. § 371 of International Patent Application No. PCT/US2019/050626, filed Sep. 11, 2019, which claims the benefit of priority under 35 U.S.C. § 119(e) to U.S. Provisional Patent Application No. 62/730,269, filed in the U.S. Patent and Trademark Office on Sep. 12, 2018, the entire contents of which are incorporated herein by reference.

STATEMENT REGARDING FEDERALLY-SPONSORED RESEARCH

This invention was made with government support awarded under Grant Number GM104986, awarded by the National Institutes of Health. The government has certain rights in the invention.

TECHNICAL FIELD

In one aspect, systems and methods are provided that detect ongoing patient pain using functional near-infrared spectroscopy.

BACKGROUND

Chronic pain or ongoing pain is well known to affect behavior, quality of life, daily function, and sometimes mobility due to being a pain that is persistent for a longer period of time. For example, with chronic pain, the pain signals are transmitted to the brain even after an injury is healed. Since pain is subjective and typically varies for different subjects, it is difficult for a physician or other medical practitioner to pinpoint when such pain occurs when a subject is unable to clearly communicate a level of pain. Typically, grimacing, moaning, movement, or the like can be indicative of a pain experienced by a subject. However, when a subject is unable to communicate or has difficulties in verbal or motor expressions, such indicators may not be available.

There are many different causes for chronic pain, such as, a prior injury, an underlying health condition, a surgical procedure, or the like. For example, many patients report having experienced pain during invasive medical procedures which may cause ongoing pain. Various approaches for assessing pain during a surgical procedure have been developed including autonomic measures which include measuring heart rates, blood pressure, and the like and a bispectral index (BIS) monitor. However, the autonomic measures provide delayed and undifferentiated response, may not be feasible in all surgical settings, and are also subjective as they rely on an anesthesiologist's experience. Additionally, the BIS monitoring is electroencephalography based and merely measures a level of anesthesia as opposed to the pain itself. Such inadequate control of the pain during a surgical procedure may result in negative outcomes such as increased postoperative pain and opioid demand.

Today chronic pain is typically treated to reduce pain and improve mobility. However, there is no current objective detection of ongoing pain. Accordingly, a technique is required that provides an objective method of assessing a subject's pain even when a subject is unable to communicate.

SUMMARY

We now provide new ongoing pain recognition systems and methods utilizing a functional near-infrared spectroscopy system. In particular, brain activity is used to determine when a subject is experiencing pain and to observe which areas of the brain are involved. These techniques also allow for prediction of treatment outcome in personalized pain management.

Preferred systems and methods are configured to detect ongoing pain using near-infrared spectroscopy (NIRS) system by obtaining functional near-infrared spectroscopy imaging data from a non-responsive patient to recognize ongoing pain in the patient. For example, this data may be obtained during a surgical procedure. In particular systems and methods, the patient is non-responsive, particularly non-responsive to commands, such as in a controlled state of anesthesia or an unconscious sedated state, or is otherwise non-responsive to commands, such as may be exhibited by a comatose patient, an infant, and the like.

In additional particular aspects, systems and methods are provided that detect pain based on pain indicia or control data obtained from a subject. This indicia or control data may be e.g. suitably obtained to a patient or subject who is conscious. For example, pain can be detected by a responsive patient or subject through any number of exercises. The patient then may be rendered non-responsive (e.g. through sedation), and the control data or pain indicia is then employed to monitor and recognize pain in the unresponsive patient.

In preferred aspects, the NIRS system can probe or detect changes in brain hemodynamic responses using infrared light wherein changes in the relative concentration of oxygenated and deoxygenated hemoglobin in the cortex indicates pain experienced by a subject, such as a patient undergoing a medical procedure.

Preferred methods include obtaining or capturing imaging data from subject, e.g. a nonresponsive patient, over a period of time (e.g. up to about 0.1, 0.5, 1, 2, 3, 5 or 10 minutes, or more) using near-infrared spectroscopy. Particularly preferred methods include obtaining or capturing optical imaging data from at least one cortical region of the brain of a subject, e.g. a non-responsive patient, over a period of time (e.g. up to about 0.1, 0.5, 1, 2, 3, 5 or 10 minutes, or more) using functional near-infrared spectroscopy. In addition, using the imaging data, preferred methods may include measuring a plurality of hemodynamic parameters, which may include oxygenated hemoglobin (HbO), deoxygenated hemoglobin (HbR), and/or total hemoglobin (HbT), in the at least one cortical region of the brain of the non-responsive patient and by observing the low frequency changes in the signals. Additionally, the method may include averaging the measured plurality of hemodynamic parameters to reduce background noise. A pattern may also be identified in the averaged hemodynamic parameters which may be compared to at least one predetermined pattern associated with patient pain. When a similarity is detected between the pattern and the predetermined pattern, a signal may be output indicating patient pain. In addition, measuring the hemodynamic parameters may include measuring oxygenated and deoxygenated hemoglobin to measure blood flow.

Preferred methods may include performing an analysis exercise such as a variation of thermal stimulus on a responsive patient (e.g. a healthy, conscious patient) to inflict a level of pain. In addition, the predetermined pattern that indicated pain may comprise a plurality of peaks in the blood flow over time, wherein the method may include determining whether a time delay between performing the various activities (e.g., the variation of thermal stimulus) and the point at which a peak occurs indicates patient pain.

Additionally, preferred systems may include a functional near-infrared spectroscopy configured to capture at least one cortical region of the brain of the patient over a period of time and a processor. The cortical region of the brain may be the medial prefrontal cortex. The processor may be configured to measure a plurality of hemodynamic parameters, which may include oxygenated hemoglobin, deoxygenated hemoglobin, and/or total hemoglobin, in the cortical region of the brain of the patient, using the optical imaging data. That is, using the imaging data, one or more hemodynamic parameters may be measured in the at least one cortical region of the brain of the non-responsive patient by converting the obtained fNIRS imaging data to cortical hemoglobin (HbO, HbR, or HbT) concentration changes and fractional power spectral density time courses. Thus, alterations in the power or fractional power of low-frequency hemodynamic oscillations are observed. In the following text, we use fractional power to illustrate our design.

Furthermore, the processor may be configured to average the measured hemodynamic parameters to reduce background noise and then may identify a pattern in the averaged hemodynamic parameters. The processor may then compare the pattern to at least one predetermined pattern associated with patient pain and detect a similarity between the pattern and the predetermined pattern. Additionally, the processor may be configured to output a signal indicating patient pain. The processor may be configured e.g. to control an analysis exercise such as a variation of thermal stimulus on the patient to inflict a level of pain toward the patient from which measurements may be obtained. Further, the processor may be configured to determine whether a time delay between performing the analysis exercise such as the variation of thermal stimulus and a point when an alteration in the fractional power of hemodynamic oscillation occurs which indicates pain in the patient.

Methods are also provided that evaluate a treatment and include administering, by a processor, the treatment toward a chronic pain patient or a patient during a surgical procedure. Such methods also may include acquiring, with a functional near-infrared spectroscopy, imaging data during the surgical procedure. Furthermore, from the imaging data, brain activity data representing a hemodynamic parameter in at least one cortical region of the brain of the patient may be determined. The brain activity data may then be compared, by the processor, to control data which may be acquired using the functional near-infrared spectroscopy prior to the imaging data and further outputting an indication of patient pain. Particularly, a return of the hemodynamic parameters in the imaging data towards the control data may indicate a relative efficiency of the treatment as a pain-relieving treatment.

Other aspects of the invention are disclosed infra.

BRIEF DESCRIPTION OF THE DRAWINGS

The disclosure will hereinafter be described with reference to the accompanying drawings, wherein like reference numerals denote like elements, and:

FIGS. 5A-5D illustrate exemplary graphs of PSD time courses and a comparison between conditions according to an exemplary embodiment of the present disclosure;

FIGS. 6A-6C illustrate exemplary graphs of recorded imaging data during a surgical procedure while the patient was under general anesthesia according to an exemplary embodiment of the present disclosure;

DETAILED DESCRIPTION

The present disclosure provides a system and method for measuring neuronal activity in cortical brain regions related to pain sensation. Such a technique allows for the ability to assess ongoing pain of patients unable to communicate or having difficulties in verbal or motor expressions. In particular, the present disclosure is capable of measuring ongoing pain using fNIRS, a non-invasive optical imaging method using near infrared light. The fNIRS provides a measure of cortical hemodynamics as oxygenated hemoglobin (HbO) and deoxygenated hemoglobin (HbR) concentration changes. Examples of such ongoing pain include neuropathic pain, inflammatory pain, and other chronic pain conditions which linger for a longer period of time.

Methods and systems of the invention are particularly useful for a wide variety of medical procedures, including where a patient is sedated to an unconscious or unresponsive state. Notably, the present invention is not limited to medical procedures and the detection of ongoing pain is useful in any treatment of chronic pain such as in a rehabilitative treatment or the like. The discussion of a medical procedure is merely exemplary.

The present pain detection systems and methods can provide continuous monitoring of neural activity related to experienced pain such as, during medical or surgical procedures. The present systems and methods also may provide control of analgesic load to improve patient intraoperative comfort and decrease postoperative pain. In addition, the measure or detection of ongoing pain may be used to evaluate the effectiveness of pharmaceuticals or other therapeutic treatments for a variety of conditions.

Preferably functional near-infrared spectroscopy (fNIRS) is employed for imaging of the patient. Functional near-infrared spectroscopy allows for functional imaging of brain activity (or activation) through monitoring of blood oxygenation and blood volume, including in patient's cortex. Imaging can be performed in the near-infrared range such as between 650-1000 nm.

According to an exemplary embodiment, in particular methods and systems, the patient is in a non-responsive state, such as an unconscious sedated state as may be controlled by administration of anesthesia, and/or may be characterized by partial or complete loss of protective nerve reflexes, including the ability to independently breathe and respond to commands The patient may be unable to cooperate and may have labile (fluctuating) vital signs. As referred to herein, an unresponsive patient or subject includes a subject exhibiting one or more characteristics of: 1) under the administration of anesthesia and non-responsive to commands, 2) partial or complete loss of protective nerve reflexes, such as loss of ability to i) respond to commands and/or ii) independently breathe. An unresponsive patient also may include patients in a coma or infants (who cannot respond to verbal commands).

Methods and systems of the invention also may be utilized for subject in a conscious state, including a conscious, awake, and healthy state. As referred to herein, a patient in a conscious state, a responsive state or other similar term is 1) capable of rational responses and/or 2) does not have altered respiratory, cardiac, and/or reflex functions (nerve reflexes from the brain) to the level that requires external support for these vital functions.

In a preferred method for recognizing ongoing pain in a non-responsive patient, steps may include obtaining functional near-infrared spectroscopy imaging data from at least one cortical region of the brain of the non-responsive patient; and comparing measured imaging data with patient pain based on control data and thereby recognizing ongoing pain in the non-responsive patient. This imaging data may be obtained during, for example, a surgical procedure, but is not limited thereto. Using the imaging data, one or more hemodynamic parameters may be measured in the at least one cortical region of the brain of the non-responsive patient by converting the obtained fNIRS imaging data to cortical hemoglobin (HbO, HbR, or HbT) concentration changes and fractional power spectral density time courses. That is, alterations in fractional power of low frequency hemodynamic oscillations are observed to thus detect the pain.

Such preferred methods may suitably comprise one or more additional steps of (i) averaging the measured plurality of hemodynamic parameters e.g. to reduce background noise; (ii) identifying a pattern in the averaged hemodynamic parameters; and/or (iii) outputting a signal indicating patient pain.

In a particular preferred method of the invention for recognizing ongoing pain in a non-responsive patient, steps may comprise obtaining functional near-infrared spectroscopy imaging data from at least one cortical region of the brain of the non-responsive patient; measuring, by a processor, using the imaging data, a plurality of hemodynamic parameters in the at least one cortical region of the brain of the non-responsive patient; averaging, by the processor, the measured plurality of hemodynamic parameters e.g. to reduce background noise; identifying, by the processor, a pattern in the averaged hemodynamic parameters; comparing, by the processor, the pattern to at least one predetermined pattern associated with patient pain based on control data; detecting, by the processor, a similarity between the pattern and the predetermined pattern; and outputting, by the processor, a signal indicating patient pain.

Additionally, the obtained functional near-infrared spectroscopy imaging data may be converted to cortical hemoglobin (HbR, HbO, or HbT) concentration changes and fractional power spectral density time courses. The hemodynamic parameters include one or more of oxygenated hemoglobin, deoxygenated hemoglobin, and total hemoglobin. Measuring at least one hemodynamic parameter may include measuring, by the processor, oxygenated and deoxygenated hemoglobin to measure blood flow. The at least one cortical region of the brain may be the medial prefrontal cortex. A predetermined pattern indicating pain may comprise a plurality of sequential peaks in blood flow over time. The at least one predetermined pattern associated with pain may be obtained from the control data for the hemodynamic parameter wherein pain is detected in a responsive patient. The control data may include measured brain signal changes during a preoperative or resting state.

Further, the functional near-infrared spectroscopy imaging data of a responsive subject may be obtained while continuously delivering a thermal pain stimulus to the patient. The functional near-infrared spectroscopy imaging data of the responsive subject may be obtained first during a resting state and then while the thermal pain stimulus is continuously applied to the responsive subject to thus detect at which point the subject experiences pain. In other words, the perception of pain in a conscious state may be used as control data for comparison of data obtained while the subject is non-responsive.

In another particular method for evaluating a therapeutic treatment after detecting ongoing patient pain, steps may comprise administering a treatment, such as a nerve block, morphine, or the like to a patient; acquiring functional near-infrared spectroscopy imaging data during the surgical procedure; determining from the imaging data, brain activity data representing a hemodynamic parameter in at least one cortical region of the brain of the patient; comparing the brain activity data representing the hemodynamic parameter to control data representing the hemodynamic parameter; and outputting an indication of patient pain. One or more of such steps may be accomplished through use of a processor. For example, the therapeutic treatment may be administered in addition to a general anesthesia during a surgical procedure to thus suppress the detected ongoing pain. Such an application of a therapeutic treatment allows for the efficacy of analgesic methods to be evaluated. That is, this allows for prediction of treatment outcome to provide a personalized pain management.

Referring now to the non-limiting exemplary drawings, various pain and sensory pathways may be measured in the brain using the NIRS system. The NIRS uses infrared light to probe changes in brain hemodynamic response, wherein near infrared light penetrates in the tissues and may traverse matter within the skull to the cortex area. A change in the relative concentration of the oxygenated hemoglobin and the deoxygenated hemoglobin in the cortex indicates a change in the number of photons that are escaping the brain.

Figure 2:
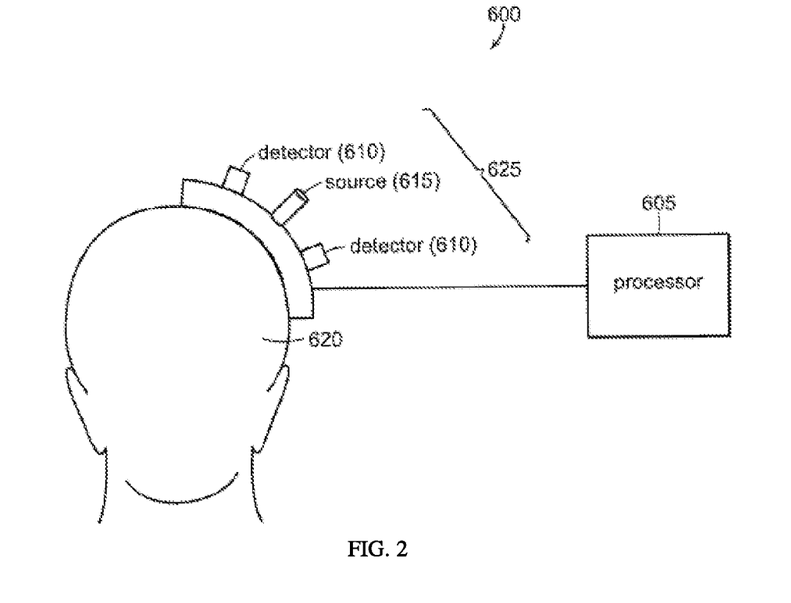
FIG. 2 illustrates an exemplary schematic diagram of the system that recognizes pain in a patent according to an exemplary embodiment of the present disclosure.

Specifically, as illustrated in FIG. 2, a functional near-infrared spectroscopy system (NIRS) 625 is a portable, non-invasive inexpensive method of monitoring hemodynamic activity at moderate depths (e.g., surface cortices). The NIRS 625 is configured to characterize relative changes in concentrations of oxygenated hemoglobin (HbO) and deoxygenated hemoglobin (HbR), which combined indicate relate change in total hemoglobin (HbT). The NIRS optodes may be fitted across predetermined cortical regions to thus monitor the hemodynamic functions caused by neuronal activity. Furthermore, since an NIRS 625 is not influenced by environmental requirements, the system may be used within an operating room. Specifically, the NIRS 625 is configured to deliver photons using fiber optics that are positioned on the head 620 of a patient and are called the source 615. In addition, other fiber cables, detectors 610, are spaced apart from the source 615 to collect the photons that are reflected from the cortical tissue. Furthermore, various detected signals may be measured to detect the intensity, the modulation depth, and the phase delay and a combination thereof may provide information regarding physiological parameters.

Furthermore, as illustrated in FIG. 2, the pain recognition system 600 may be configured to capture optical imaging data from at least one cortical region of the brain over a period of time, using the NIRS system 625. In addition, the system 600 may include a processor 605 that may be configured to measure a plurality of hemodynamic parameters in the at least one cortical region of the brain of the non-responsive patient, using the optical imaging data. In particular, the processor 605 may be configured to convert the obtained imaging data to cortical oxy-hemoglobin concentration changes and fractional power spectral density time courses to thus compare the data with patient pain based on control data.

The control data may be obtained by fitting the NIRS 625 system to a patient that is responsive and healthy. That is, data may be collected from the responsive patient while a thermal stimulus is applied to the patient. Data may be collected at point where the patient indicates experiencing pain, while the patient is conscious (e.g., is not sedated). Thus, when a patient is sedated, the control data may act as an indication of points where pain is known to exist or be experienced by the patient. Moreover, the hemodynamic parameters may include oxygenated hemoglobin, deoxygenated hemoglobin, and total hemoglobin. In addition, the at least one cortical region of the brain may be the medial prefrontal cortex. The processor 605 may be further configured to control a variation of thermal stimulus on the patient to inflict a level of pain from which measurements may be obtained. Furthermore, the processor 605 may be configured to determine a time delay between performing the analysis exercise such as the variation of thermal stimulus and a point when an alteration in the fractional power of hemodynamic oscillation occurs which indicates pain in the patient.

Figure 1:
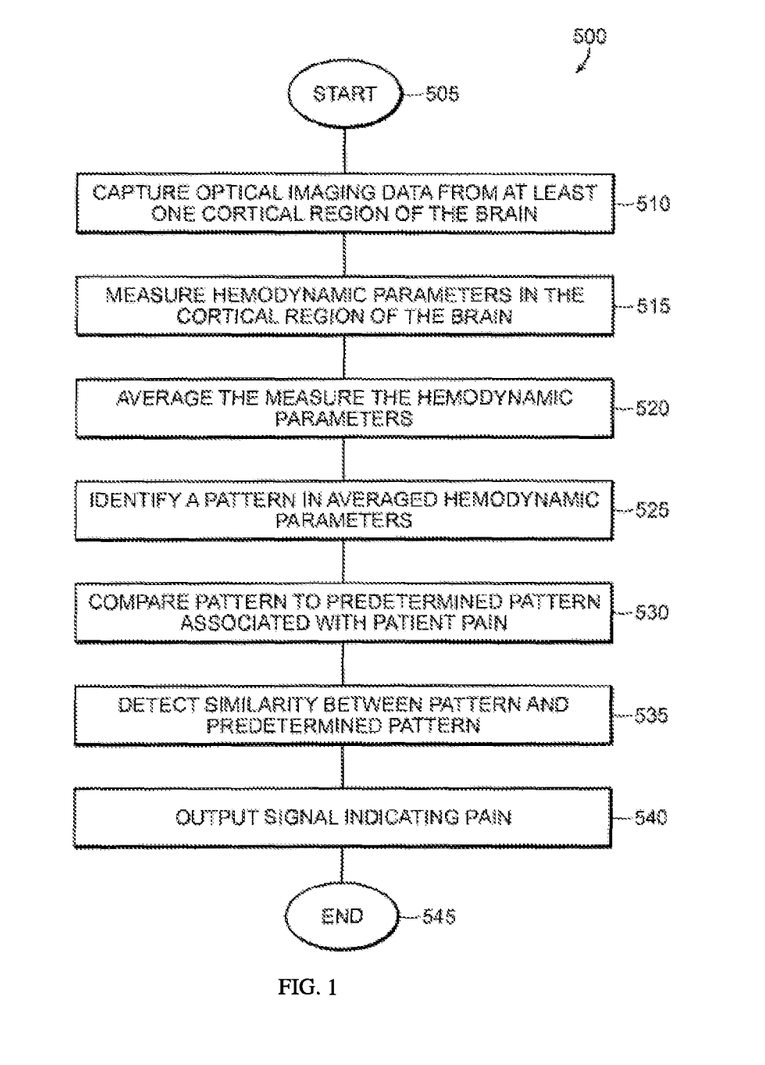
FIG. 1 illustrates an exemplary flowchart of the method that recognizes pain in a patient according to an exemplary embodiment of the present disclosure.

Moreover, FIG. 1 illustrates an exemplary flowchart of process 500 of recognizing ongoing pain in a patient. The process 500 may illustratively start at 505 and continue to 510 wherein optical imaging data may be captured from at least one cortical region of the brain of the non-responsive patient over a period of time, using a functional near-infrared spectroscopy. Furthermore, the process includes in 515 measuring, by a processor, a plurality of hemodynamic parameters in the at least one cortical region of the brain of the non-responsive patient, using the optical imaging data. This process of measuring the hemodynamic parameters is further illustrated in FIG. 8. That is, FIG. 8 illustrates the NIRS data pre-processing and frequency analysis of the NIRS signals.

In 520, the process may include averaging, by the processor, the measured plurality or hemodynamic parameters to reduce background noise and in 525, identifying, by the processor, a pattern in the averaged hemodynamic parameters. In addition, in 530, the process may include comparing, by the processor, the pattern to at least one predetermined patter associated with patient pain. The process may then include in 535, detecting, by the processor, a similarity between the pattern and the predetermined pattern. Lastly, in 540, outputting, by the processor, a signal indicating patient pain, and then the processor may illustratively end in 545.

Figure 8:
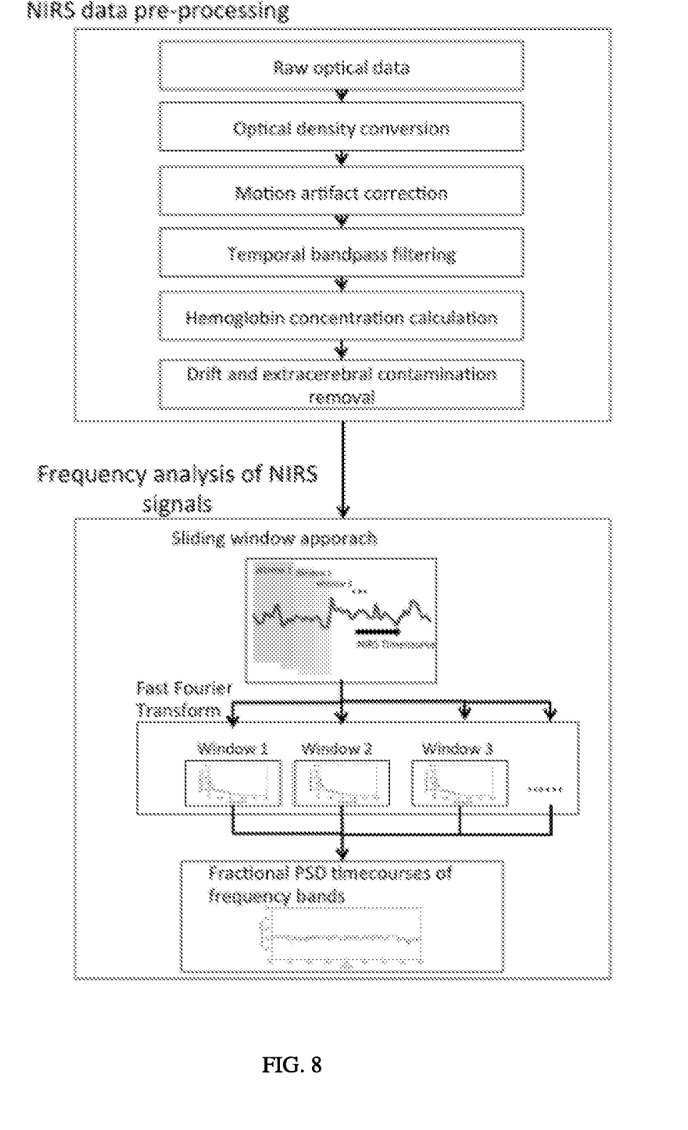
FIG. 8 illustrates an exemplary flowchart of NIRS data processing algorithm to extract power frequency density parameters in the cortical region of the brain according to an exemplary embodiment of the present disclosure.

The process may further include converting the obtained fNIRS imaging data to cortical hemoglobin (HbO, HbR, or HbT) concentration changes and fractional power spectral density time courses to thus observe the changes in the low frequency signals, as shown in FIG. 8. Although, HbO shows a highest signal-to-noise ratio, HbR and HbT concentrations may also be used.

Furthermore, the hemodynamic parameters may include oxygenated hemoglobin, deoxygenated hemoglobin, and total hemoglobin. The measuring of the hemodynamic parameter may include measuring, by the processor, the time and frequency properties of oxygenated and deoxygenated hemoglobin concentration changes to measure blood flow. The at least one cortical region of the brain may be selected from the somatosensory cortex the prefrontal cortex, and lateral parietal cortex.

Furthermore, the at least one predetermined pattern associated with pain may be obtained from control data for the hemodynamic parameter, wherein the control data may be obtained by acquiring the optical imaging data form the at least one cortical region of the brain of a conscious patient. Specifically, the control data may be obtained when a stimulus has not been administered to a patient (e.g., a resting state) and includes performing, by the processor, an activity to the patient. The activity performed on the patient may include a variation of thermal stimulus to inflict pain. This stimulus may be applied to the patient a plurality of times to evoke different pain perceptions. In addition, the process may include, administering, by the processor, an anesthetic regimen based on a particular medical procedure toward the patient after obtaining the control data.

In a further embodiment of the present disclosure, a method that evaluates a treatment (e.g., a therapeutic treatment) may include administering, by a processor, the treatment toward a chronic pain patient or a patient during a surgical procedure. Furthermore, the process may include acquiring imaging data and determining, by the processor, brain activity data representing hemodynamic parameter in a least one cortical region of the brain of the patient, from the imaging data and comparing, by the processor, the brain activity data representing the hemodynamic parameter to control data representing the hemodynamic parameter. The process may further include outputting, by the processor, an indication of patient pain. Additionally, the process may include acquiring, by the processor, control data using the functional near-infrared spectroscopy prior to obtaining the activity imaging data. Particularly, a return of the hemodynamic parameters in the imaging data towards the control data indicates a relative efficiency of the treatment as a pain-relieving treatment.

Methods and systems of the invention may be employed to detect ongoing pain and the following non-limiting examples are illustrative of the invention.

EXAMPLE

In regards to detection of ongoing pain, a study was conducted in which alterations in fractional power of low frequency hemodynamic oscillations were observed mainly from the medial prefrontal cortex. In particular, using fNIRS, changes in cortical hemodynamic oscillations were measured related with the ongoing pain. These alterations were associated with experimental pain stimuli in healthy subjects or subjects with painful surgical procedures such as knee arthroscopy surgery. The observations were conducted under both awake and anesthetized conditions.

In the healthy subjects, two scans were conducted. The first scan was a resting state scan in which the subject was asked to sit in a chair and relax. The second scan was an ongoing pain scan in which the subject continuously received thermal pain stimulus on dorsum of the hand for about 5 to 6 minutes.

In the surgical subjects, a scan was conducted in the resting state (e.g., preoperative state) where brain signal changes were measured. Additionally, a scan was conducted where brain signal changes were measured during the knee arthroscopy surgery while under general anesthesia.

Figure 3:
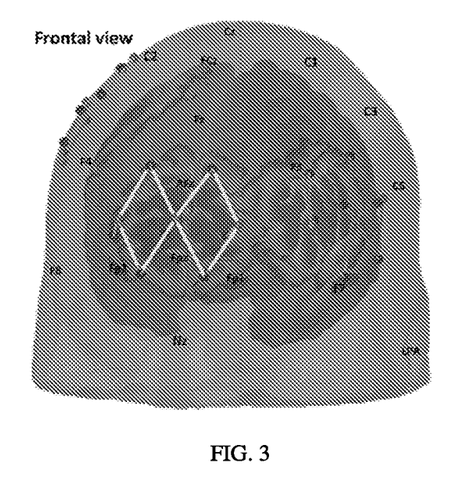
FIG. 3 illustrates a view of the fNIRS optode arrangement according to an exemplary embodiment of the present disclosure.
Figure 4:
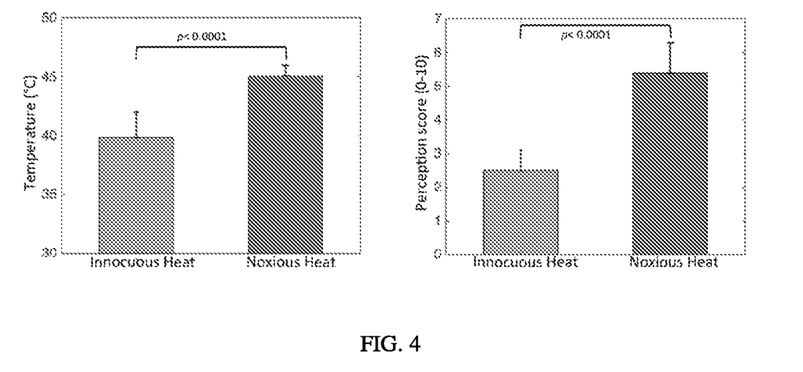
FIG. 4 illustrates an exemplary graphs of applied thermal stimuli to a responsive patient and corresponding perception levels according to an exemplary embodiment of the present disclosure.
Figures 5A, 5D:
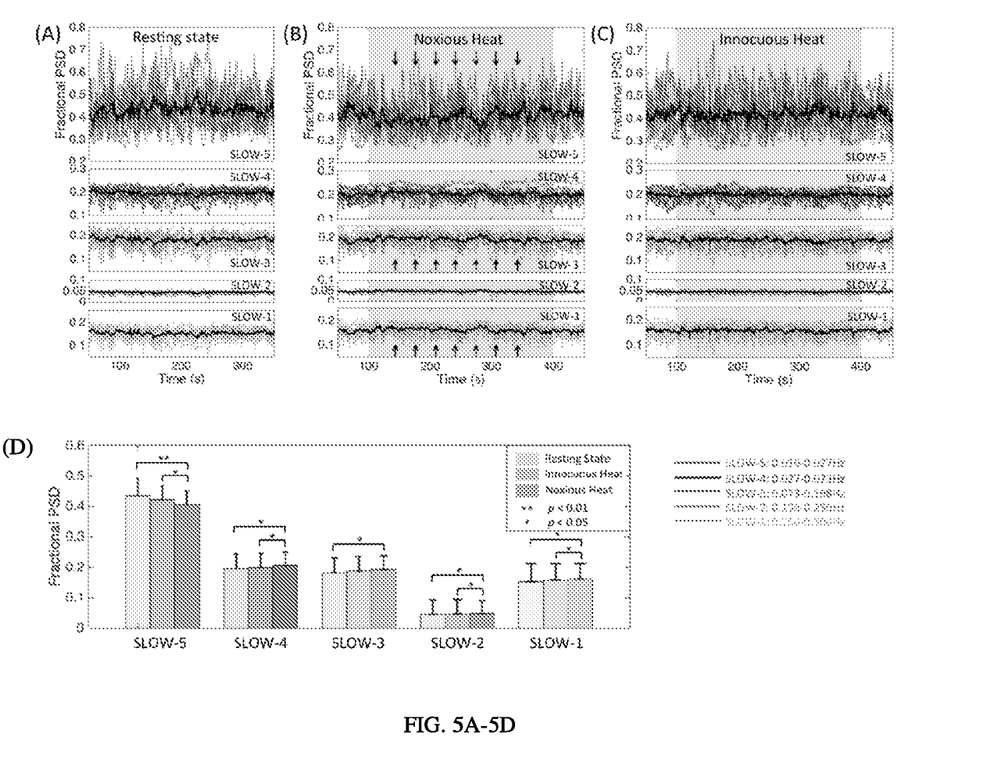

The fNIRS signals were collected, as shown in FIG. 3, and then converted to cortical oxy-hemoglobin (HbO) concentration changes and to fractional power spectral density time courses. Particularly, FIG. 3 shows the fNIRS optode arrangement used in this study. Data was captured and analyzed from the mPFC channels. The HbO changes were generated using a Matlab toolbox HOMER2 and the fractional power spectral density time courses were generated using Fast Fourier Transform and a sliding window approach, as shown in FIG. 8. That is, FIG. 8 illustrates the process of collecting raw optical data and the conversion to fractional power spectral density time courses. The analysis focused on five sub-bands of the low frequency hemodynamic oscillations SLOW-5 (0.01-0.027 Hz), SLOW-4 (0.027-0.073 Hz), SLOW-3 (0.073-0.198 Hz), SLOW-2 (0.198-0.25 Hz), and SLOW-1 (0.25-0.50 Hz).

Results

The results of these scans for patients under general anesthesia in both healthy subjects and those undergoing surgical procedures showed a decreased fractional power in lower frequency hemodynamic signals (e.g., 0.01-0.027 Hz) and an increased fractional power in the higher frequency hemodynamic signals (e.g., 0.027 Hz-0.50 Hz) from the medial prefrontal cortex.

Particularly, in the healthy patients, as shown in FIGS. 4 and 5A-5D, a decreased fractional power in the lower frequency hemodynamic signals (e.g., SLOW-5) and an increased fractional power in the higher frequency hemodynamic signals (e.g., SLOW-3 to SLOW-1) were observed from the mPFC signals associated with ongoing experimental pain where the patient continuously received a thermal stimulus.

Figures 6A, 6C:
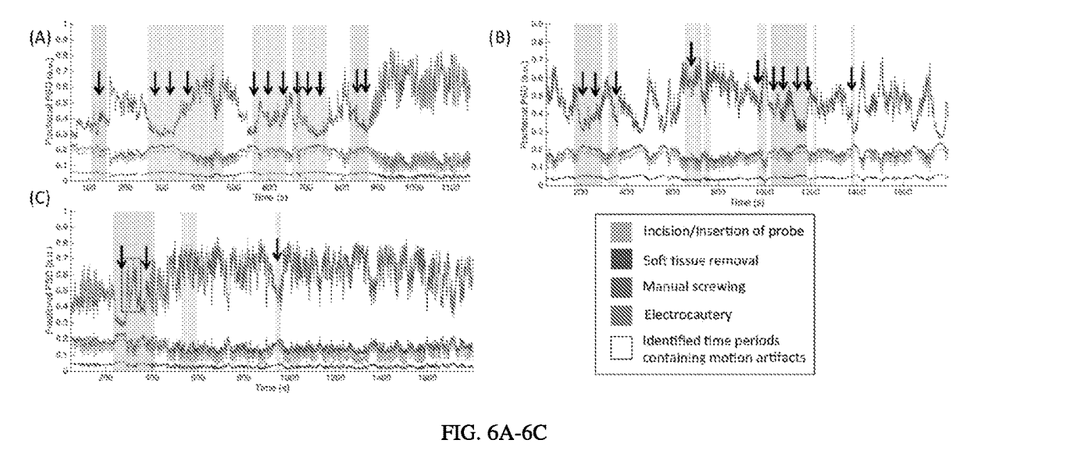

In the surgical patients, as shown in FIGS. 6A-6C, similar power shifts were observed from lower frequency bands to higher frequency bands in the low frequency hemodynamic oscillations of the mPFC associated with surgical procedures (e.g., causing ongoing pain). The black arrows shown in these graphs represent the time when a power shift from lower sub-bands to higher sub-bands was observed.

Figure 7:
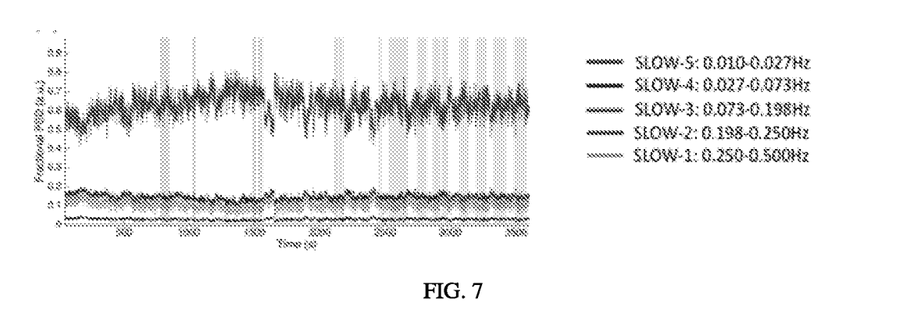
FIG. 7 illustrates an exemplary graph of data during a surgical procedure while the patient was under general anesthesia and an additional effective nerve block according to an exemplary embodiment of the present disclosure.

Notably, once an ongoing pain was detected in a surgical patient, the efficacy of analgesic methods to suppress such ongoing pain was also evaluated. For example, some patients received an effective nerve block in addition to the anesthesia. As shown in FIG. 7, the power shifts after the surgical procedure were observed to be modulated by the analgesic effect. That is, in the patients that received the effective nerve block, much less significant power shifts in the low frequency hemodynamic oscillations were observed following the surgical procedure.

These above-discussed results provide a biomarker for using fNIRS to detect ongoing pain under both awake and anesthetized conditions.

The present pain detector apparatus and methods can provide continuous monitoring of neural activity related to pain experienced during medical procedures. That apparatus may provide control of analgesic load to improve patient intraoperative comfort and decrease postoperative pain. In addition, the measure or detection of ongoing pain may be used to evaluate the effectiveness of pharmaceuticals for a variety of conditions.

What is claimed is:

1. A method of detecting ongoing pain in a non-responsive patient, comprising:
   placing a functional near-infrared spectroscopy system (NIRS) onto at least one cortical region of the brain of the non-responsive patient;
   obtaining function near-infrared spectroscopy (fNIRS) imaging data from the at least one cortical region of a brain of the non-responsive patient using the NIRS;
   comparing measured imaging data with patient pain based on control data and thereby recognizing pain in the non-responsive patient by converting the obtained fNIRS imaging data to cortical hemoglobin concentration changes using fractional power spectral density time courses to observe frequency changes; and
   controlling an analgesic load delivered to the non-responsive patient as a result of the comparing step.

2. The method of claim 1, wherein the imaging data is obtained during a surgical procedure, and/or wherein the control data include measured brain signal changes during a preoperative state, and/or wherein the fNIRS imaging data is collected while the non-responsive patient is under general anesthesia.

3. The method of claim 1, wherein the obtained imaging data is used to measure one or more hemodynamic parameters in the at least one cortical region of the brain of the non-responsive patient.

4. The method claim 1, wherein the control data includes pain indicia detected in the patient while responsive and/or wherein the control data is obtained by acquiring optical imaging data from the at least one cortical region of the brain of a responsive patient.

5. The method of claim 1, wherein the optical imaging data is acquired by performing an activity to the patient, wherein the activity includes delivery of a physiological stimulus to the patient.

6. The method of claim 5, wherein the thermal pain stimulus is delivered to the patient during three stages including a first stage as a resting state, a second stage of delivering an innocuous thermal stimulus, and a third stage of delivering a noxious thermal stimulus.

7. A method of detecting ongoing pain in a non-responsive patient, comprising:
   placing a functional near-infrared spectroscopy system (NIRS) onto at least one cortical region of the brain of the non-responsive patient;
   obtaining function near-infrared spectroscopy (fNIRS) imaging data from the at least one cortical region of the brain of a responsive patient and the non-responsive patient using the NIRS;
   comparing the imaging data of each of the responsive patient and the non-responsive patient with control data by converting the obtained fNIRS imaging data to cortical hemoglobin concentration changes using fractional power spectral density time courses to observe frequency changes; and
   controlling an analgesic load delivered to the non-responsive patient as a result of the comparing step.

8. The method of claim 7, wherein the obtaining of fNIRS imaging data of the responsive patient includes:
   obtaining fNIRS imaging data during a resting state;

continuously delivering pain stimulus to patient; and
obtaining fNIRS imaging data during the delivery of the thermal pain stimulus.

9. The method of claim 7, wherein the obtaining of fNRIS imaging data of the non-responsive patient includes:
collecting fNIRS imaging data during a preoperative state; and
collecting fNIRS imaging data while the non-responsive patient is under anesthesia or sedation during a surgical procedure.

10. The method of claim 9, further comprising:
converting the obtained fNIRS imaging data to cortical hemoglobin concentration changes and fractional power spectral density time courses.

11. The method of claim 10, further comprising:
comparing the data of the non-responsive patient with the data of the responsive patient to detect ongoing pain in the patient during the surgical procedure.

12. The method of claim 11, further comprising:
in response to detecting ongoing pain in the patient during the surgical procedure, assessing a therapeutic effect on the at least one cortical region of the brain by administering a therapeutic treatment to the non-responsive patient; and
conducting a plurality of function near-infrared spectroscopy (fNIRS) scans to detect patient pain.

13. The method of claim 12, wherein the administering of a plurality of fNIRS scans includes:
conducting a fNIRS scan prior to administration of the therapeutic treatment; and
continuously conducting a fNIRS scan during the surgical procedure after administration of the therapeutic treatment.

14. The method of claim 13, further comprising:
acquiring fNIRS imaging data from each scan during the delivery of the stimuli;
determining from the imaging data, brain activity data representing a hemodynamic parameter in the cortical region of the brain of the patient; and
comparing the brain activity data representing the hemodynamic parameter to the control data that represents the hemodynamic parameter; and
outputting an indication of patient pain.

15. A system that detects ongoing pain in a non-responsive patient comprising:
a functional near-infrared spectroscopy system (NIRS) configured to capture optical imaging data from at least one cortical region of the brain of the non-responsive patient; and
a processor configured to:
measure, using the optical imaging data measured by the NIRS, a plurality of hemodynamic parameters in the at least one cortical region of the brain of the non-responsive patient; and
compare measured imaging data with patient pain based on control data and thereby recognizing pain in the non-responsive patient by converting the obtained fNIRS imaging data to cortical hemoglobin concentration changes using fractional power spectral density time courses to observe frequency changes; and
control an analgesic load delivered to the non-responsive patient as a result of the processor compare step.

16. The system of claim 15, wherein the imaging data is obtained during a surgical procedure.

17. The system of claim 15, wherein the control data include measured brain signal changes during a preoperative state.

18. The method of claim 5, wherein the physiological stimulus is a variation of thermal pain stimulus.

19. The method of claim 9, wherein collecting fNIRS imaging data while the non-responsive patient is under anesthesia or sedation during a surgical procedure includes:
collecting fNIRS imaging data while the non-responsive patient is under general anesthesia.

20. The method of claim 8, wherein the continuously delivering pain stimulus to patient includes:
continuously delivering thermal pain stimulus to the patient.

* * * * *